United States Patent [19]

Seymour et al.

[11] 4,098,602
[45] Jul. 4, 1978

[54] ALGAECIDAL COMPOSITION

[75] Inventors: Donald E. Seymour, Milwaukee; James C. Schmidt, Wauwatosa; Donald A. Bezella, Saukville, all of Wis.

[73] Assignee: Applied Biochemists, Inc., Mequon, Wis.

[21] Appl. No.: 700,334

[22] Filed: Jun. 28, 1976

[51] Int. Cl.$^2$ .................. A01N 9/02; A01N 13/00
[52] U.S. Cl. ........................................... 71/67
[58] Field of Search ........................................ 71/67

[56] References Cited

U.S. PATENT DOCUMENTS

| 2,734,028 | 2/1956 | Domogalla | 71/67 |
| 2,878,155 | 3/1959 | Cruickshank | 71/67 |
| 3,634,061 | 1/1972 | Geiger et al. | 71/67 X |
| 3,716,351 | 2/1973 | Kunkel et al. | 71/67 |
| 3,905,797 | 9/1975 | Kunkel et al. | 71/67 X |
| 3,930,834 | 1/1976 | Schulteis et al. | 71/67 |

FOREIGN PATENT DOCUMENTS 2,506,431  9/1975  Fed. Rep. of Germany ........... 71/67

Primary Examiner—Joseph Paul Brust
Attorney, Agent, or Firm—Andrus, Sceales, Starke & Sawall

[57] ABSTRACT

An algaecidal composition comprising the combination of an ammonium quaternary compound and a copper complex formed by reacting a copper compound with a complexing material, such as an alkanolamine, a tertiary amine, a diamine, ammonium hydroxide, or a polyethylene glycol. The algaecidal composition has extended stability and shelf-life and possess improved algaecidal effectiveness.

7 Claims, No Drawings

ALGAECIDAL COMPOSITION

BACKGROUND OF THE INVENTION

Copper ions are known to be effective against the growth of algae. In the past water-soluble copper compounds, such as copper sulfate, have been used extensively as algaecides. Copper ions released by copper sulfate when added to water, react with carbonates or bicarbonates found in water to produce insoluble copper compounds which precipitate and cause turbidity or cloudiness in the treated water. If excessive amounts of insoluble copper compounds settle out, the compounds can form a sludge, which in the case of a lake or stream, may tend to destroy the fish life or zooplankton which is essential as fish food.

To overcome the problems associated with the use of copper sulfate, a complex formed by the reaction of copper sulfate and an alkanolamine, as disclosed in U.S. Pat. No. 2,734,028, has been used and has achieved wide success as an algaecide. A complex of this type has the ability to maintain the copper ions in solution, even when the algaecide is added to alkaline water containing high concentrations of carbonates or bicarbonates, as well as soft water situations.

It has been found that a copper complex of the type disclosed in U.S. Pat. No. 2,734,028 tends to decompose when subjected to sunlight and/or warm temperatures resulting in a precipitation of copper, thereby removing the toxic copper ions from solution and decreasing the effectiveness of the complex as an algaecide. To avoid the problems associated with the use of the complex derived from copper sulfate, a copper complex has been prepared using water insoluble copper compounds as disclosed in U.S. Pat. No. 3,930,834. In this latter patent the complex is formed by initially reacting an insoluble copper compound with an acid in aqueous solution to dissociate the copper ions and thereafter chelating the released copper ions to form the complex.

The copending U.S. patent application Ser. No. 700,335, filed June 28, 1976 now abandoned, discloses an improved method of preparing a copper complex from water insoluble copper compounds in which the copper compound is reacted with a chelating material, preferably an alkanolamine. The chelating material acts to solubilize and chelate the copper compound to form the copper complex.

Ammonium quaternary compounds are known for their fungicidal, bacteriacidal and algaecidal properties and have been used in the past for controlling the growth of pathogenic microorganisms in hospitals, dairies, laundries, restaurants, and the like, as well as being used to control algae in water treating systems and cooling towers.

SUMMARY OF THE INVENTION

The invention relates to an algaecidal composition having particular use for controlling the growth of algae in artificial bodies of water, such as swimming pools. The composition comprises the combination of an ammonium quaternary compound and a copper complex preferably formed by the process disclosed in the copending U.S. patent application Ser. No. 700,335 filed June 28, 1976. In general, the copper complex is formed by reacting a water insoluble soluble copper compound with a complexing material, such as an alkanolamine, a tertiary amine, a diamine, ammonium hydroxide, or a polyethylene glycol.

The composition of the invention has superior compatability and has extended stability and shelf-life over prior algaecidal compositions.

The combination of the ammonium quaternary compound and the copper complex formed by the above recited method produces an algaecidal composition that is particularly effective against highly resistant strains of algae encountered in swimming pools, such as blue-green algae, and the composition exhibits synergistic efficacy as compared to either of the separate components of the composition.

DESCRIPTION OF THE PREFERRED EMBODIMENT

The invention is directed to an algaecidal composition comprising the combination of an ammonium quaternary compound and a copper complex formed as disclosed in the copending U.S. patent application Ser. No. 700,335, filed June 28, 1976, The quaternary compound can comprise from 5% to 95% by weight of the combination with the copper complex being the balance, based on 100% active ingredients.

The ammonium quaternary compound is preferably a salt having the following formula:

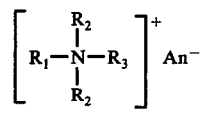

where $R_1$ is an alkyl radical having 8 to 20 carbon atoms or a radical of the formula:

where $R_4$ is an alkyl group having 8 to 20 carbon atoms; each $R_2$ is an alkyl group containing 1 to 2 carbon atoms; and $R_3$ is a methyl, ethyl, allyl or benzyl radical. An- represents the anion.

Specific ammonium quaternary compounds which can be used are n-alkyl (60% $C_{14}$, 30% $C_{16}$, 5% $C_{12}$, 5% $C_{18}$) dimethyl benzyl ammonium chloride, n-alkyl (68% $C_{12}$, 32% $C_{18}$) dimethyl benzyl ammonium chloride, dialkyl (8% $C_8$, 9% $C_{10}$, 47% $C_{12}$, 18% $C_{14}$, 8% $C_{16}$, 10% $C_{18}$) dimethyl ammonium chloride, dialkyl (24% $C_{16}$ 76% $C_{18}$) dimethyl ammonium chloride, n-alkyl (50% $C_{12}$, 30% $C_{14}$, 17% $C_{16}$, 3% $C_{18}$) dimethyl ethyl benzyl ammonium chloride, n-alkyl (8% $C_8$, 9% $C_{10}$, 47% $C_{12}$, 18% $C_{14}$, 8% $C_{16}$, 10% $C_{18}$) trimethyl ammonium chloride, methyl dodecyl benzyl trimethyl ammonium chloride, methyl dodecyl xylylene bis-trimethyl ammonium chloride, alkyl (90% $C_{12}$, 9% $C_{14}$, 1% $C_{18}$) trimethyl ammonium chloride, diisobutyl phenoxyethoxy ethyl dimethylbenzyl ammonium chloride, diisobutyl cresoxy ethoxy ethyl dimethylbenzyl ammonium chloride, poly[oxyethylene (dimethyliminio) ethylene (dimethyliminio) ethylene dichloride], and mixtures thereof. Other halides, such as bromides, can be substituted for the chlorides.

The copper complex is formed as disclosed in the aforementioned United States patent application and the disclosure of that patent application is incorporated by reference herein.

In general, the copper complex is prepared by reacting a powdered or finely divided water insoluble copper compound with a complexing or chelating material, which acts to solubilize and chelate the copper compound. The water insoluble copper compound can take the form of copper carbonate, copper hydroxide, copper benzoate, copper oxide, copper bicarbonate, copper thiocyanate, copper oxychloride, tri basic copper sulfate (a water insoluble mixture of copper hydroxide and copper sulfate), and the like.

The complexing or chelating material can take the form of alkanolamines having one or more alkanol groups containing 1 to 10 carbon atoms, tertiary amines, diamines, ammonium hydroxide and polyethylene glycols having an average molecular weight of 200 to 4000. For examples of alkanolamines that can be used are monoethanolamine, aminoethylethanolamine, diethanolamine, triethanolamine, dimethylethanolamine, diethylethanolamine, monoisopropanolamine, diisopropanolamine, triisopropanolamine, methyldiethanolamine, and the like. The diamines can take the form of ethylene diamine and N,N,N',N', tetrakis(2-hydroxypropyl) ethylene diamine, and the like.

The alkanolamines are preferred as the chelating material, and the combination of monoethanolamine and trimethanolamine is particularly effective in solubilizing and chelating the copper compound, because the chelation occurs in a relatively short period of time and the resulting copper complex is particularly stable to hydrolysis. While other of the listed chelating materials will effect chelation, longer time periods may be required.

The chelating material can be used either as a 100% active material or in solution, preferably aqueous solution. In most cases, aqueous solution is used as it accelerates the reaction and provides a cost reduction. The concentration of the solution, however, is not critical and can vary within wide limits.

The chelating material is generally used in a weight ratio of 1 to 10 parts per part of the copper compound based on 100% active ingredients.

The complex is prepared by adding the powdered or finely divided copper compound to the chelating material and employing gentle mixing or stirring. Elevated temperatures are not required, although with some copper compounds elevated temperatures up to 180° F are preferred in order to accelerate the solution.

The resulting copper complex has a pH generally in the range of about 8.0 to 11.0 and can contain up to about 20% by weight of elemental copper, and generally above 8.5% elemental copper.

The ammonium quaternary compound and the copper complex are preferably mixed together in aqueous solution. Heating is not required to form the solution although gentle heating can be utilized, if desired.

The combination of the ammonium quaternary compound and the copper complex is particularly effective against resistant strains of algae encountered in swimming pools, such as blue-green algae as for example, Phormidium, Lyngbya, Oscillatoria, and Aphanizomenon. The combination produces an unusual and synergistic action against such algae. Algae of this type has an outer gelatinous sheath which resists penetration by the toxic copper ions and it is believed that the quaternary compound breaks down the gelatinous sheath so that the copper ions can penetrate the algae cell to kill the algae. Thus, the combination of ingredients cooperate and are more effective against this type of algae than either of the individual ingredients used alone.

The composition of the invention is normally stored, handled, and transported as a concentrate containing about 50% to 80% by weight of the active ingredients and the balance being a carrier or solvent, such as water. The concentrated solution is normally diluted at the time of use in the ratio of 5 to 50 parts of water to each part of the concentrated solution. The diluted solution is applied to the body of water so that the body of water contains from 1.0 to 6.0 ppm by weight of the active ingredients.

Copper complexes formed by the use of water soluble copper compounds, such as copper nitrate, copper sulfate, and copper acetate, can be used in combination with, or in place of, the copper complex formed by the method of the aforementioned patent application. The soluble copper compound in aqueous solution is reacted with a complexing or chelating material, as described above, to form the complex. The copper complex derived from the water soluble copper compounds should have a pH above 7.6, and preferably above 8.5, when combined with the ammonium quaternary compound.

The following examples illustrate the method of preparing the algaecidal composition of the invention.

EXAMPLE I 1.65 lbs. of copper carbonate were added at 75° F to 3.86 lbs. of water along with 2.04 lbs. of monoethanolamine and 2.53 lbs. of triethanolamine. The resulting copper complex contained 9.0% of elemental copper.

2.88 lbs. of the copper complex were added to 5.54 lbs. of 80% n-alkyl (50% $C_{14}$, 40% $C_{12}$, 10% $C_{16}$) dimethyl benzyl ammonium chloride. The resulting solution contained 3.07% of elemental copper and 52.68% of the quaternary material.

EXAMPLE II 1.71 lbs. of tri-basic copper sulfate, 0.27 gal. of triethanolamine and 0.24 gal. of monoethanolamine were added to 0.46 gal. of water. The resulting copper complex contained 9.0% elemental copper 0.286 gal. of this copper complex was mixed with 0.714 gal. of an 80%, 50:50 mixture of n-alkyl (60% $C_{14}$, 30% $C_{16}$, 5% $C_{12}$, 5% $C_{18}$) dimethyl benzyl ammonium chloride and n-alkyl (68% $C_{12}$, 32% $C_{14}$) dimethyl ethylbenzyl ammonium chloride. The resulting solution contained 3.07% of elemental copper and 52.68% of the quaternary compounds.

EXAMPLE III 1.40 lbs. of copper hydroxide, 0.24 gal. of monoethanolamine and 0.27 gal. of triethanolamine were added to 0.48 gal. of $H_2O$ at 75° F. The resulting complex contained 9.0% elemental copper.

0.265 gal. of the copper complex was mixed with 0.735 gal. of poly[oxyethylene (dimethyliminio) ethylene (dimethyliminio) ethylene dichloride] and the resulting solution contained 2.47% by weight of elemental copper and 43.51% by weight of the quaternary compound.

EXAMPLE IV 1.82 lbs. of copper sulfate was dissolved in 0.69 gal. of $H_2O$ and 0.12 gal. of monoethanolamine and 0.14 gal. of triethanolamine were added to the solution at 75° F to form the copper complex containing 4.6% by weight of elemental copper.

0.286 gal. of the complex was mixed with 0.714 gal. of 80% n-alkyl (68% $C_{12}$, 32% $C_{14}$) dimethyl ethylbenzyl ammonium chloride, and the resulting solution contained 1.55% by weight of elemental copper and 52.83% by weight of the quaternary compound.

Various modes of carrying out the invention are contemplated as being within the scope of the following claims particularly pointing out and distinctly claiming the subject matter which is regarded as the invention.

We claim:

1. A method of controlling the growth of an algae in a body of water, comprising the step of contacting algae in a body of water with a composition consisting essentially of an aqueous solution having dissolved therein (a) an ammonium quaternary compound and (b) a copper complex, said copper complex being formed by reacting a water insoluble copper compound selected from the group consisting of copper carbonate, copper hydroxide, copper bicarbonate, copper oxide, copper thiocyanate, copper oxychloride, tri basic copper sulfate, and mixtures thereof, with a material selected from the group consisting of alkanolamines having one or more alkanol groups containing 1 to 10 carbon atoms, ethylene diamine, N,N,N',N', tetrakis(2-hydroxy-propyl)ethylene diamine, ammonium hydroxide, and polyethylene glycols having an average molecular weight of 200 to 4000, said ammonium quatarnary compound being a salt having the following formula:

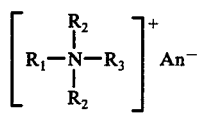

where $R_1$ is an alkyl radical having 8 to 20 carbon atoms or a radical of the formula:

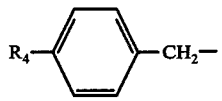

where $R_4$ is an alkyl group having 8 to 20 carbon atoms; each $R_2$ is an alkyl group containing 1 to 2 carbon atoms, $R_3$ is a methyl, ethyl, allyl, or benzyl radical and An⁻ is an anion, said ammonium quaternary compound comprises from 5% to 95% by weight of the combination and the copper complex comprises the balance, based on 100% active ingredients.

2. The method of claim 1, wherein said material comprises a mixture of monoethanolamine and triethanolamine.

3. An algaecidal composition, comprising an algaecidal affect amount of the combination of (a) an ammonium quaternary compound and (b) a copper complex, said copper complex being formed by reacting a water insoluble copper compound selected from the group consisting of copper carbonate, copper hydroxide, copper bicarbonate, copper oxide, copper thiocyanate, copper oxychloride, tri basic copper sulfate, and mixtures thereof, with a material selected from the group consisting of alkanolamines having one or more alkanol groups containing 1 to 10 carbon atoms, ethylene diamine, N,N,N',N',tetrakis(2-hydroxy-propyl) ethylene diamine, ammonium hydroxide, and polyethylene glycols having an average molecular weight of 200 to 4000, said ammonium quaternary compound being a salt having the following formula:

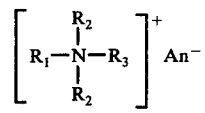

where $R_1$ is an alkyl radical having 8 to 20 carbon atoms or a radical of the formula:

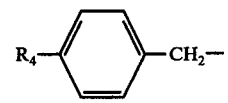

where $R_4$ is an alkyl group having 8 to 20 carbon atoms; each $R_2$ is an alkyl group containing 1 to 2 carbom atoms; $R_3$ is a methyl, ethyl, allyl, or benzyl radical and An⁻ is an anion, said ammonium quaternary compound comprises from 5% to 95% by weight of the combination and the copper complex comprises the balance, based on 100% active ingredients.

4. The composition of claim 3, wherein said material comprises a mixture of monoethanolamine and triethanolamine.

5. The composition of claim 3, wherein said ammonium quaternary compound and said copper complex are in aqueous solution.

6. The composition of claim 5, wherein said aqueous solution contains from about 50% to 80% by weight of active ingredients.

7. An algaecidal composition, comprising an algaecidal affect amount of the combination of (a) an ammonium quaternary compound and (b) a copper complex, said copper complex being formed by reacting a water insoluble copper compound selected from the group consisting of copper carbonate, copper hydroxide, copper bicarbonate, copper oxide, copper thiocyanate, copper oxychloride, tri basic copper sulfate, and mixtures thereof, with a material selected from the group consisting of alkanolamines having one or more alkanol groups containing 1 to 10 carbon atoms, ethylene diamine, N,N,N',N',tetrakis(2-hydroxy-propyl) ethylene diamine, ammonium hydroxide, and polyethylene glycols having an average molecular weight of 200 to 4000, said ammonium quaternary compound being poly[oxyethylene(dimethyliminio)ethylene(dimethyliminio) ethylene dichloride], said ammonium quaternary compound comprises from 5% to 95% by weight of the combination and the copper complex comprises the balance, based on 100% active ingredients.

* * * * *

UNITED STATES PATENT AND TRADEMARK OFFICE
CERTIFICATE OF CORRECTION

PATENT NO. : 4,098,602
DATED : July 4, 1978
INVENTOR(S) : DONALD E. SEYMOUR ET AL It is certified that error appears in the above-identified patent and that said Letters Patent are hereby corrected as shown below:

Column 1, Line 65, Cancel "soluble" and substitute therefor ---insoluble---, Column 6, Line 25, CLAIM 3, Cancel "carbom" and substitute therefor ---carbon---

Signed and Sealed this

Thirteenth Day of February 1979

[SEAL]

Attest:

RUTH C. MASON
Attesting Officer

DONALD W. BANNER
Commissioner of Patents and Trademarks